United States Patent
Gould et al.

(10) Patent No.: US 6,923,647 B2
(45) Date of Patent: Aug. 2, 2005

(54) METHOD FOR REMOVING A DENTAL CROWN AND APPARATUS THEREFOR

(76) Inventors: Gordon Gould, 113 Brennans Moor, Water Mill, NY (US) 11976; Jack Goodman, 1415 Crabhouse Rd., Lusby, MD (US) 20657; Abraham Ingber, 9249 Cambridge Manor Ct., Potomac, MD (US) 20854

(*) Notice: Subject to any disclaimer, the term of this patent is extended or adjusted under 35 U.S.C. 154(b) by 18 days.

(21) Appl. No.: 10/870,612

(22) Filed: Jun. 17, 2004

(65) Prior Publication Data

US 2004/0229190 A1 Nov. 18, 2004

Related U.S. Application Data

(63) Continuation of application No. 10/230,282, filed on Aug. 29, 2002, now abandoned.

(51) Int. Cl.[7] .............................. A61C 3/16; A61C 1/07
(52) U.S. Cl. ..................... 433/116; 433/215; 433/119
(58) Field of Search .................... 433/118, 119, 433/121, 148, 153, 215

(56) References Cited

U.S. PATENT DOCUMENTS

| | | |
|---|---|---|
| 3,332,149 A | 7/1967 | Mumaw |
| 3,332,150 A | 7/1967 | Mumaw |
| 3,742,605 A | 7/1973 | Cooper |
| 3,889,376 A | 6/1975 | Zatkin |
| 4,127,125 A | 11/1978 | Takemoto et al. |
| 4,219,619 A | 8/1980 | Zarow |
| 4,725,233 A | 2/1988 | Planert |
| 4,772,202 A | 9/1988 | Ebner, Jr. |
| 5,106,302 A | 4/1992 | Farzin-Nia et al. |
| 5,269,291 A | 12/1993 | Carter |
| 5,320,532 A | 6/1994 | Farzin-Nia et al. |
| 5,451,736 A | 9/1995 | Fiedler et al. |
| 5,547,380 A | 8/1996 | Goodman |
| 6,171,107 B1 | 1/2001 | Milne |
| 6,437,334 B1 | 8/2002 | Thomas et al. |

FOREIGN PATENT DOCUMENTS

| | | |
|---|---|---|
| DE | 41 09 988 | 10/1992 |
| FR | 2 534 134 | 4/1984 |
| WO | WO 2004/019805 | 3/2004 |

*Primary Examiner*—Ralph A. Lewis
(74) *Attorney, Agent, or Firm*—Eric P. Schellin

(57) ABSTRACT

Method and tool for fracturing the cement interface between a crown and a tooth or the like. The method is accomplished by positioning a piezoelectric driven rapid impacting tool against one side of a portion of a crown covering the tooth. The tool is covered with a malleable metal and is interfacing abutment with said crown. The opposite side of the crown is abutted against an anvil which is covered with a thicker malleable metal interface.

3 Claims, 2 Drawing Sheets

METHOD FOR REMOVING A DENTAL CROWN AND APPARATUS THEREFOR

This application is a Continuation of U.S. application Ser. No. 10/230,282 filed Aug. 29, 2002 and now abandoned.

FIELD OF THE INVENTION

The present invention relates to a dental tool and method of use, and more particularly, to a tool for fracturing the interface between two dental structures that have been adhesively secured together.

BACKGROUND OF THE PRESENT INVENTION

Dental structures such as caps, crowns and bridges are bonded to natural tooth roots or implanted posts by well known conventional cements. It is equally well known, that the removal of cemented dental structures may be necessary for one or more of the following reasons:

(a) The occurrence of dental decay.
(b) To examine the vitality and pulpal involvement of an underlying tooth
(c) To repair cemented dental structures made defective by the wear of materials.
(d) The loss of selected supporting teeth.

It is also known that natural tooth roots are connected to bone structure by a matrix of connecting fibers. It is stated that the connecting fibers exhibit a resultant vector force which holds the tooth root in place, which vector force operates substantially along a longitudinal axis in the direction of the top to bottom of the tooth. Thus, properly directed impacting forces permit the use of short force magnitude but of high frequency to break or fracture the cement bonds holding the dental structure to the tooth root with a minimal detrimental effect to the fibers or natural tooth roots.

In the prior art, removal of dental structures such as caps, crowns and bridges was accomplished by often times sacrificing the tooth bearing the caps, crown or bridge or by the application of a rigid grasping means to the structure followed by a manual application of an impacting or leverage force in an attempt to break the cement bonds. However, prior art devices could apply only in exact magnitudes of impacting forces since manual means were used. Such manual means were further limited in that the oral cavity is not large enough to permit easy direct impacting to those dental structures located near the rear of the oral cavity. Other consequences of the use of prior art apparatuses are patient discomfiture, and inconvenience to the dentist occasioned by the cumbersome mechanical apparatus.

Some recent progress has been made by the use of diminutive ultrasonic probes for application to teeth to remove or loosen orthodontics and other dental structures, such as disclosed in U.S. Pat. Nos. 5,106,302 and 5,320,532 to Farzin-Nia et al.

Even more recently the art for removal of crowns and the like has been considerably advanced by the invention disclosed in U.S. Pat. No. 5,547,300 to Goodman, the material therein is incorporated herein in its entirety.

SUMMARY OF THE INVENTION

It is accordingly an object of the present invention to provide a more efficient apparatus for the removal of cemented dental structures.

It is another object of the invention to provide an apparatus for the removal of a cemented dental structure using precisely impacting forces directed essentially transversely to the longitudinal axis of said structure.

It is still another object of this invention to provide an apparatus for the removal of a cemented dental structure operable in confined regions of the oral cavity.

It is an object of this invention to provide an automatic apparatus thereby minimizing manual intervention for effecting the removal of a cemented dental structure.

It is another object of this invention to provide an apparatus for the removal of a cemented dental structure which apparatus includes a clamping means to hold the dental structure.

It is still another object of this invention to provide a piezoelectric transducer apparatus for the removal of a cemented structure wherein the piezo crystals are affixed to at least longitudinally extending sides of a steel core.

It is yet another object of this invention to provide a piezoelectrically driven device in a clamp wherein the steel core terminates in an impacting cone. The said cone has a thin copper cap affixed thereto. An anvil is provided and secured to the clamp and a thicker copper cap is affixed to the anvil. The crown is secured therein between.

It is yet another object of this invention to provide apparatus for the removal of a cemented dental structure which apparatus may be selectively coupled to any of a plurality of so-called permanent cap, crown or bridge structures.

The direction of application of impacting must be applied perpendicular to the plane of the cement of the structure. In this way the bond of the cement is fractured by shocking it with numerous low power but nevertheless high frequency shock waves. In use, the piezoelectric device with a cone covered with a thin copper shield is placed perpendicular to the axis of the tooth, at proximate the open end of the cap. The opposite side of the cap must be backed by an anvil. A thicker copper shield is positioned between the cap and the anvil as stated in the foregoing.

Preferably the anvil and the piezoelectric tool is positioned at the confronting legs of a vise-like device whereby the cap of the tooth is positioned there between in a gripping manner. The vise action results in maintaining constant contact of the piezoelectric tool through the thinner copper shield with the cap or crown which inhibits considerably the production of sound by the piezoelectric tool of the present invention, thereby making it more pleasant for the patient.

An important feature of the present invention resides in the fact that as the impacts occur from the piezoelectric tool, the copper shields become work hardened but not before it becomes conformed to the surface of the cap or crown that is being impinged.

The concept is to preferably flex the rim area of the cap or crown very rapidly after work hardening the copper shields but with a minimum of lateral displacement, of the order of approximately five microns whereby the cement is trapped and fractured between the inertia of the root or post on the flexing cap. It has been discovered that the fracture line begins at the point of abutment of the copper sheathed cone of the piezoelectric tool and extends around the tooth, post or root to the other side of the cap or crown. This greatly reduces the energy and time required to break the bond. There is no deleterious pulling force on the tooth, only tiny vibrations. Since there is no pulling or tugging on the tooth and the motion is small, large caps even with multiple posts or roots are loosened by fracturing the cement at each bond individually.

DETAILED DESCRIPTION OF THE INVENTION

Figure 1:
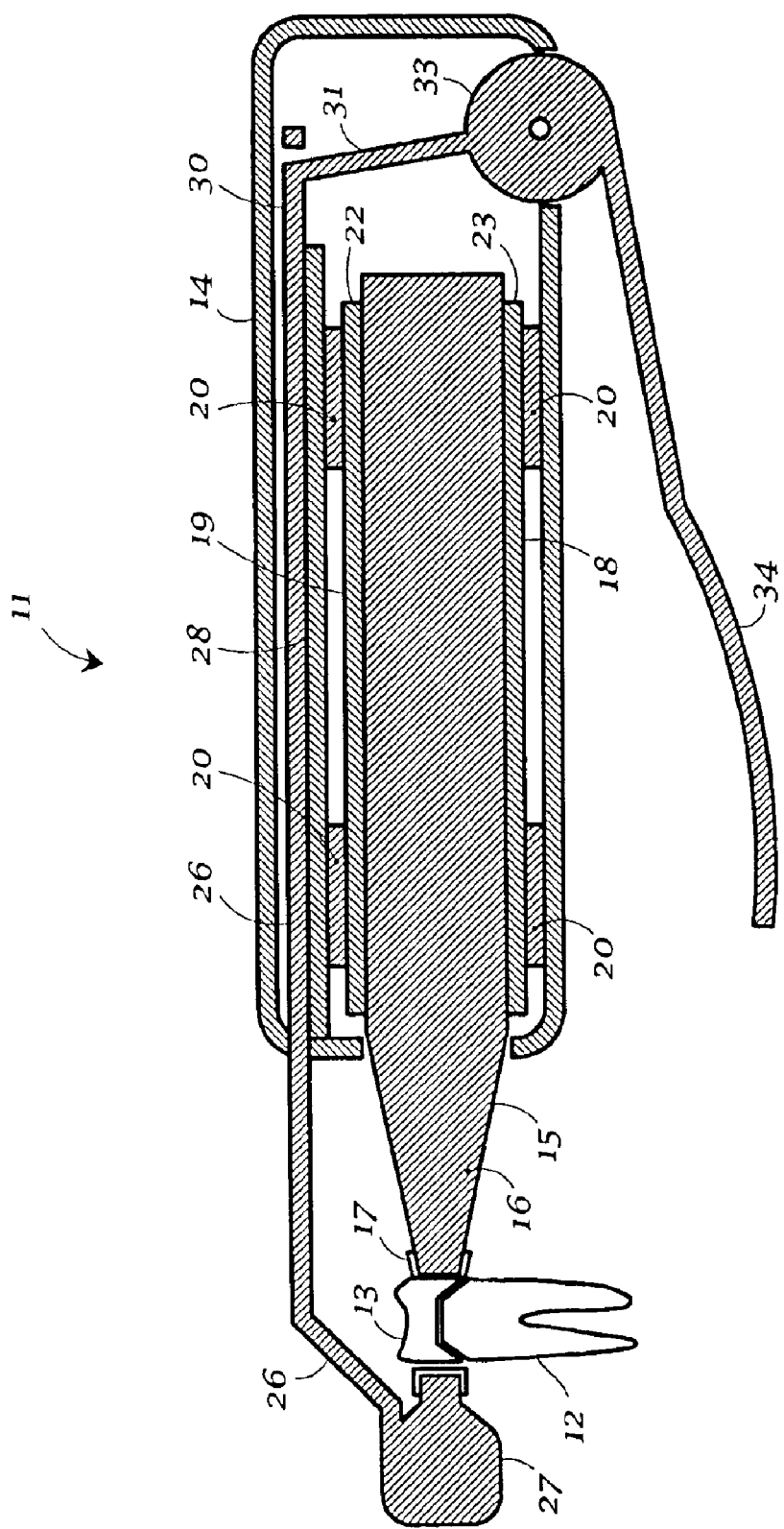
FIG. 1 is a schematic of the clamp in a side elevation.
Figure 3:
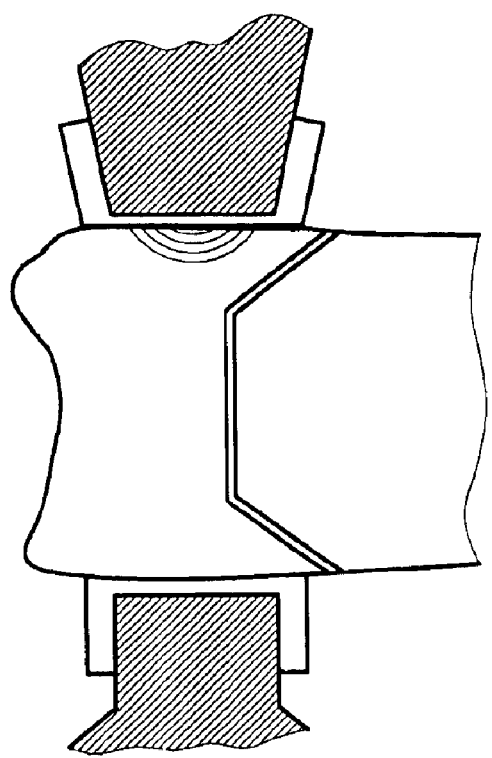
FIG. 3 is the same view as in FIG. 2 with the fracture in progress.

Attention is now directed to FIG. 1 where the device is shown, generally, at 11 which is depicted as being clamped about a tooth 12 which has a cap 13 thereon. The device 11 has a housing 14 which has mounted therein a piezoelectric device 15 consisting of an elongated steel four sided bar 16 that terminates in a truncated cone portion 17 at its distal end. The bar 16 has mounted on opposite surfaces piezoelectric crystals 18 and 19. These crystals are adhesively secured to the bar 16 by a conventional epoxy cement. The bar 16 and the piezoelectric crystals 18 and 19 are mounted in the housing 14 by rubber mounts 20. The piezoelectric crystals 18 and 19 are electrically connected to a source of electricity by electrically conducting wires 22 and 23.

The housing 14 has an elongated linearly spaced channel 25 in which is mounted a reciprocable movable metal flat member 28. The distal end 26 thereof terminates in an anvil portion 27 which is confrontingly mounted in regard to the truncated cone portion 17 and spaced therefrom detailed to accommodate the to-be treated crown or cap of a tooth.

The proximate end 30 of flat member 28 is operatively connected to an arm 31 which is arcuately mounted to hub 33. The hub 33 has an elongated handle 34. An operator grasps in one hand both the housing 14 and the handle 34. When the housing 14 and the handle 34 are squeezed together the anvil 27 moves linearly in the direction of the truncated cone 17. A tooth 12 with a to-be removed cap 13 is grasped between the anvil 27 and the truncated cone 17.

Figure 2:
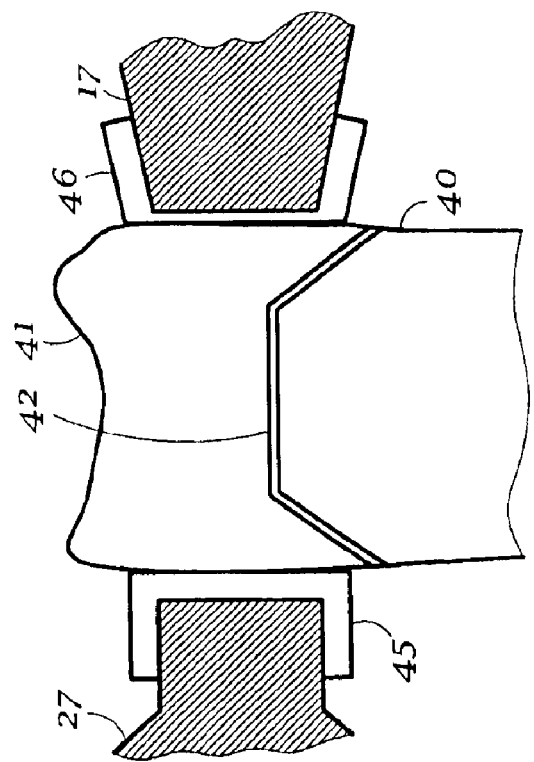
FIG. 2 is a schematic showing the device of the invention employed with the crown in part in cross section.

Attention is now directed to FIG. 2 which depicts in fragmentary details a tooth 40 having a crown 41 and a cement 42 there between. Positioned between the crown 42 and the anvil 27 is a cup 45 of relatively thick copper. At the truncated cone 17 is a thinner cup copper interface 46. Copper is the preferred material as it is very malleable. A combination of the clamping between the anvil and the truncated cone and the vibrations afforded by the piezoelectric device results in the copper surfaces touching the crown 41 conform to the surfaces of the crown 41. The copper cup 45 being thicker results in good holding characteristics while the thinner copper cup 46 on the truncated cone 17 permits the delivery of vibrations in a manner to spread the peak pressure.

The vibrations set up in the crown concentrate on the cement pulverizing it in situ with fracturing spreading in a ripple effect throughout the cement resulting in a complete loosening of the crown ready for subsequent removal.

It is submitted that a similar and applicable piezoelectric tool construction can be seen in U.S. Pat. No. 5,269,291 to Carter. This patent is incorporated herein in its entirety.

Once the fracturing has been completed the device 10 can be removed, followed by the removal of the cap 41. In the infrequent event that the fracturing is incomplete the device may be re-positioned for further impact impingement. At no time with the method of the invention is it necessary to apply pulling forces on the crown or tooth which can result in loosening of the tooth per se.

It is to be understood that various other changes and modifications may be made without departing from the scope of the present invention. The present invention being only limited by the claims.

What is claimed is:

1. A method for disintegrating the cement which adheres a crown to a tooth thereby loosening the crown for removal comprising the steps of:

proving an adjustable clamp, wherein said clamp has two legs, one leg having a piezoelectric device comprising an elongated metal bar and having opposing flat surfaces, at least two of said opposing flat surfaces having piezoelectric crystals adhesively secured thereto, said metal bar terminating in a truncated cone, said truncated cone being covered by a first malleable shield;

said other leg being an anvil which is covered by a second malleable shield whereby the said crown that is to be loosened is between said first shield and said second shield and said shields are in abutment with opposite sides of said crown when said device is being employed;

activating said piezoelectric device to impinge lateral strokes through said first shield against said crown whereby said first shield and said second shields are work hardened;

controlling the lateral strokes of the piezoelectric device whereby lateral motion imparted to said crown is less than 10 microns, whereby causing a disintegration of the cement to occur at said cap to which the piezoelectric device impinges;

permitting the said disintegration to extend to the other side of the crown while continuing the activation of the piezoelectric device until the crown is completely loosened; thereafter removing said crown.

2. The method of claim 1 wherein the malleable shields are fabricated of copper.

3. The method of claim 2 wherein the second shield on the anvil is relatively thicker than the first shield on the said truncated cone.

* * * * *